United States Patent
Prutchi et al.

(10) Patent No.: US 12,375,925 B2
(45) Date of Patent: Jul. 29, 2025

(54) SECURE SHORT-RANGE COMMUNICATIONS LINK FOR MEDICAL DEVICES

(71) Applicant: Impulse Dynamics NV, Willemstad (CW)

(72) Inventors: David Prutchi, Voorhees, NJ (US); Jason Meyers, Haddonfield, NJ (US)

(73) Assignee: Impulse Dynamics NV, Willemstad (CW)

( * ) Notice: Subject to any disclaimer, the term of this patent is extended or adjusted under 35 U.S.C. 154(b) by 338 days.

(21) Appl. No.: 17/438,437

(22) PCT Filed: Mar. 10, 2020

(86) PCT No.: PCT/IB2020/052048
§ 371 (c)(1),
(2) Date: Sep. 12, 2021

(87) PCT Pub. No.: WO2020/183355
PCT Pub. Date: Sep. 17, 2020

(65) Prior Publication Data
US 2022/0159468 A1    May 19, 2022

Related U.S. Application Data

(60) Provisional application No. 62/816,981, filed on Mar. 12, 2019.

(51) Int. Cl.
*H04W 12/122* (2021.01)
*H04B 5/00* (2024.01)
(Continued)

(52) U.S. Cl.
CPC ............ *H04W 12/122* (2021.01); *H04B 5/72* (2024.01); *H04W 12/03* (2021.01);
(Continued)

(58) Field of Classification Search
CPC .. H04B 5/0081; H04B 5/0031; H04B 5/0037; H04W 12/122; H04W 12/03;
(Continued)

(56) References Cited

U.S. PATENT DOCUMENTS 5,455,466 A    10/1995  Parks et al.
7,155,290 B2   12/2006  Von Arx et al.
(Continued)

FOREIGN PATENT DOCUMENTS

CN    101517940    8/2009
CN    103328041    9/2013
(Continued)

OTHER PUBLICATIONS

Konstantin Khramtcov Analysis of Power Supply Methods for Wireless Biomedical Sensors and Future Development Prospects; topic approved by the Faculty Council of the Faculty of Electrical Engineering on Aug. 30, 2017; pp. 1-76.*

(Continued)

*Primary Examiner* — Mohammad A Siddiqi

(57) ABSTRACT

Embodiments of communication systems are disclosed for protecting communication between an implanted device ID and an external device ED. Optionally, the ID communicates over the TET channel by modulating a load on the channel. While the ID is communicating the ED optionally adds noise to the TET channel, inhibiting malicious interception of the communication. Using knowledge of the noise signal, the ED cleans the noise from the TET signal to recover the communication from the ID. In some embodiments, the TET link is used to pass an encryption key and/or to verify communications over a radio channel. The TET channel may be authenticated. For example, authentication may include a minimum energy and/or power transfer.

23 Claims, 7 Drawing Sheets

(51) Int. Cl.
| | |
|---|---|
| *H04B 5/72* | (2024.01) |
| *H04W 12/03* | (2021.01) |
| *H04W 12/0431* | (2021.01) |
| *H04W 12/06* | (2021.01) |
| *A61N 1/372* | (2006.01) |

(52) U.S. Cl.
CPC ....... *H04W 12/0431* (2021.01); *H04W 12/06* (2013.01); *A61N 1/37252* (2013.01)

(58) Field of Classification Search
CPC .... H04W 12/0431; H04W 12/06; H04K 1/02; H04K 3/825; H04K 3/43; H04K 3/42; H04K 3/44; H04K 3/94; A61N 1/37254; A61N 1/37252
See application file for complete search history.

(56) References Cited

U.S. PATENT DOCUMENTS

| | | | |
|---|---|---|---|
| 7,587,241 B2 | 9/2009 | Parramon et al. | |
| 8,214,642 B2 | 7/2012 | Baentsch et al. | |
| 8,254,572 B2 | 8/2012 | Vaughan et al. | |
| 8,331,563 B2 | 12/2012 | Healy et al. | |
| 8,611,540 B2 | 12/2013 | Chaturvedi et al. | |
| 9,154,002 B2 | 10/2015 | Norconk et al. | |
| 9,288,614 B1* | 3/2016 | Young | A61N 1/37254 |
| 9,401,894 B2 | 7/2016 | Kalpin et al. | |
| 9,730,593 B2* | 8/2017 | Felix | A61B 5/35 |
| 9,763,087 B2 | 12/2017 | Westhues | |
| 10,252,066 B2* | 4/2019 | Radziemski | A61N 1/3787 |
| 10,456,123 B2* | 10/2019 | Hundertmark | A61B 17/0057 |
| 11,043,299 B2 | 6/2021 | Hencin | |
| 11,357,439 B1 | 6/2022 | Fischell et al. | |
| 11,589,748 B2* | 2/2023 | Maharbiz | A61B 5/686 |
| 2003/0022315 A1* | 1/2003 | Bujard | C12N 15/635 435/69.7 |
| 2005/0055244 A1 | 3/2005 | Mullan et al. | |
| 2005/0063488 A1 | 3/2005 | Troyk et al. | |
| 2005/0075694 A1 | 4/2005 | Schmeling et al. | |
| 2005/0203582 A1 | 9/2005 | Healy et al. | |
| 2006/0187015 A1* | 8/2006 | Canfield | H02J 13/00016 340/474 |
| 2007/0118188 A1 | 5/2007 | Von Arx et al. | |
| 2007/0293142 A1 | 12/2007 | Dehmas et al. | |
| 2007/0293894 A1 | 12/2007 | Zhang et al. | |
| 2008/0021972 A1 | 1/2008 | Huelskamp et al. | |
| 2008/0288029 A1 | 11/2008 | Healy et al. | |
| 2009/0063193 A1* | 3/2009 | Barton | G08B 21/02 340/539.11 |
| 2009/0270949 A1 | 10/2009 | Kalpin et al. | |
| 2010/0076524 A1 | 3/2010 | Forsberg et al. | |
| 2010/0114224 A1* | 5/2010 | Krause | A61N 1/3605 607/28 |
| 2010/0279606 A1 | 11/2010 | Hillan et al. | |
| 2011/0028855 A1 | 2/2011 | Blomqvist | |
| 2011/0135092 A1 | 6/2011 | Lehner | |
| 2011/0171905 A1 | 7/2011 | Roberts et al. | |
| 2011/0172740 A1* | 7/2011 | Matos | A61N 1/362 607/60 |
| 2012/0101397 A1 | 4/2012 | Blomqvist | |
| 2012/0174187 A1 | 7/2012 | Argon et al. | |
| 2012/0266221 A1 | 10/2012 | Castelluccia et al. | |
| 2013/0108046 A1 | 5/2013 | Andersen | |
| 2013/0110008 A1 | 5/2013 | Bourget et al. | |
| 2013/0166642 A1 | 6/2013 | Polefko et al. | |
| 2013/0181538 A1 | 7/2013 | Calasso | |
| 2014/0185805 A1 | 7/2014 | Andersen | |
| 2014/0273824 A1 | 9/2014 | Fenner et al. | |
| 2015/0142653 A1 | 5/2015 | Neumann et al. | |
| 2015/0334563 A1 | 11/2015 | Freda et al. | |
| 2016/0175600 A1 | 6/2016 | Amir et al. | |
| 2016/0199657 A1* | 7/2016 | Jiang | A61N 1/3787 607/61 |
| 2016/0213937 A1* | 7/2016 | Reinke | A61N 1/37229 |
| 2017/0095667 A1* | 4/2017 | Yakovlev | A61B 5/0022 |
| 2017/0161449 A1 | 6/2017 | Meskens | |
| 2017/0223540 A1 | 8/2017 | Battiwalla et al. | |
| 2018/0036477 A1 | 2/2018 | Olson et al. | |
| 2018/0145838 A1* | 5/2018 | Wang | H04L 9/3278 |
| 2018/0191693 A1 | 7/2018 | Juels | |
| 2019/0009097 A1* | 1/2019 | Hartley | A61N 1/37258 |
| 2019/0245681 A1* | 8/2019 | Alwen | H04L 9/085 |
| 2020/0252436 A1* | 8/2020 | Yoon | H04W 52/0229 |
| 2021/0058257 A1* | 2/2021 | Pepin | H04L 9/3247 |
| 2021/0377740 A1* | 12/2021 | Prutchi | A61N 1/37254 |
| 2023/0276242 A1 | 8/2023 | Prutchi | |

FOREIGN PATENT DOCUMENTS

| | | |
|---|---|---|
| CN | 104080513 | 10/2014 |
| CN | 106512214 | 3/2017 |
| CN | 106924878 | 7/2017 |
| CN | 107150654 | 9/2017 |
| CN | 107405083 | 11/2017 |
| CN | 108136191 | 6/2018 |
| CN | 109076084 | 12/2018 |
| DE | 102011104364 | 12/2012 |
| JP | 2002-315209 | 10/2002 |
| WO | WO 99/038272 | 7/1999 |
| WO | WO 2017/007642 | 1/2017 |
| WO | WO 2019/239343 | 12/2019 |
| WO | WO 2020/183355 | 9/2020 |

OTHER PUBLICATIONS

Communication Pursuant to Article 94(3) EPC Dated Aug. 25, 2023 From the European Patent Office Re. Application No. 20713973.4 (11 Pages).
Translation Dated Apr. 15, 2022 of Notification of Office Action Dated Mar. 18, 2022 From the State Intellectual Property Office of the People's Republic of China Re. Application No. 202080006318. 4. (12 Pages).
Translation Dated Apr. 3, 2023 of Reexamination Notice Dated Mar. 23, 2023 From the State Intellectual Property Office of the People's Republic of China Re. Application No. 202080006318.4. (24 Pages).
Notification of Office Action and Search Report Dated Aug. 29, 2022 From the State Intellectual Property Office of the People's Republic of China Re. Application No. 201980052087.8. (11 Pages).
Translation Dated Jul. 25, 2022 of Decision of Rejection Dated Jul. 4, 2022 From the China National Intellectual Property Administration Re. Application No. 202080006318.4. (7 Pages).
Notice of Allowance Dated Nov. 7, 2022 from the US Patent and Trademark Office Re. U.S. Appl. No. 16/973,822. (22 pages).
International Preliminary Report on Patentability Dated Dec. 24, 2020 From the International Bureau of WIPO Re. Application No. PCT/IB2019/054909. (10 Pages).
International Search Report and the Written Opinion Dated Nov. 8, 2019 From the International Searching Authority Re. Application No. PCT/IB2019/054909. (17 Pages).
International Search Report and the Written Opinion Dated Jul. 27, 2020 From the International Searching Authority Re. Application No. PCT/IB2020/052048. (25 Pages).
Invitation to Pay Additional Fees, Communication Relating to the Results of the Partial International Search and the Provisional Opinion Dated May 15, 2020 From the International Searching Authority Re. Application No. PCT/IB2020/052048. (17 Pages).
Invitation to Pay Additional Fees, Communication Relating to the Results of the Partial International Search and the Provisional Opinion Dated Sep. 18, 2019 From the International Searching Authority Re. Application No. PCT/IB2019/054909. (12 Pages).
Notification of Office Action and Search Report Dated Sep. 1, 2021 From the State Intellectual Property Office of the People's Republic of China Re. Application No. 201980052087.8 and Its English Summary and Claims. (20 Pages).
Notification of Office Action and Search Report Dated Oct. 9, 2021 From the State Intellectual Property Office of the People's Republic of China Re. Application No. 202080006318.4. (11 Pages).

(56) References Cited

OTHER PUBLICATIONS

Bash et al. "Hiding Information in Noise: Fundamental Limits of Covert Wireless Communication", IEEE Communications Magazine, 53(12): 26-31, arXiv:1506.00066v1, May 30, 2015.
Maurer et al. "Unbreakable Keys From Random Noise", Security With Noisy Data, Chap. 1: 21-44, 2007.
Notification of Office Action and Search Report Dated Mar. 31, 2022 From the State Intellectual Property Office of the People's Republic of China Re. Application No. 201980052087.8. (12 Pages).
Notification of Office Action Dated Mar. 18, 2022 From the State Intellectual Property Office of the People's Republic of China Re. Application No. 202080006318.4. (10 Pages).
Reexamination Notice Dated Mar. 23, 2023 From the State Intellectual Property Office of the People's Republic of China Re. Application No. 202080006318.4. (16 Pages).
English Translation Dated Apr. 29, 2022 of Notification of Office Action and Search Report Dated Mar. 31, 2022 From the State Intellectual Property Office of the People's Republic of China Re. Application No. 201980052087.8. (13 Pages).
Official Action Dated Apr. 21, 2022 from US Patent and Trademark Office Re. U.S. Appl. No. 16/973,822. (27 pages).
Notice of Reason(s) for Rejection Dated Jul. 4, 2023 From the Japan Patent Office Re. Application No. 2021-519014 and Its Translation Into English. (9 Pages).
International Preliminary Report on Patentability Dated Sep. 23, 2021 From the International Bureau of WIPO Re. Application No. PCT/IB2020/052048. (19 Pages).
Translation Dated Sep. 13, 2022 of Notification of Office Action Dated Aug. 29, 2022 From the China National Intellectual Property Administration Re. Application No. 201980052087.8. (5 Pages).
Interview Summary Dated Jun. 6, 2022 from US Patent and Trademark Office Re. U.S. Appl. No. 16/973,822. (2 pages).
Decision of Rejection Dated Jul. 24, 2022 From the State Intellectual Property Office of the People's Republic of China Re. Application No. 202080006318.4. (8 Pages).
Translation Dated Nov. 5, 2021 of Notification of Office Action and Search Report Dated Oct. 9, 2021 From the State Intellectual Property Office of the People's Republic of China Re. Application No. 202080006318.4. (6 Pages).
Official Action Dated Sep. 8, 2023 from the US Patent and Trademark Office Re. U.S. Appl. No. 18/108,688. (22 pages).
Interview Summary Dated Dec. 1, 2023 from the US Patent and Trademark Office Re. U.S. Appl. No. 18/108,688. (2 pages).
Official Action Dated May 6, 2024 from the US Patent and Trademark Office Re. U.S. Appl. No. 18/108,688. (24 pages).
Supplementary European Search Report and the European Search Opinion Dated Jul. 4, 2024 From the European Patent Office Re. Application No. 24169186.4. (8 Pages).
Requisition by the Examiner Dated Feb. 5, 2025 From the Innovation, Science and Economic Development Canada, Canadian Intellectual Property Office Re. Application No. 3,133,024. (7 Pages).
Official Action Dated Dec. 19, 2024 from the US Patent and Trademark Office Re. U.S. Appl. No. 18/108,688. (32 pages).

\* cited by examiner

SECURE SHORT-RANGE
COMMUNICATIONS LINK FOR MEDICAL
DEVICES

RELATED APPLICATIONS

This application is a National Phase of PCT Patent Application No. PCT/IB2020/052048 having International filing date of Mar. 10, 2021, which claims the benefit of priority under 35 USC § 119(e) of U.S. Provisional Patent Application No. 62/816,981 filed on Mar. 12, 2019. The contents of the above applications are all incorporated by reference as if fully set forth herein in their entirety.

FIELD AND BACKGROUND OF THE INVENTION

The present invention, in some embodiments thereof, relates to a method of securing wireless communication and, more particularly, but not exclusively, to a method of security key transfer with an implanted medical device over a near field communication channel.

U.S. Pat. No. 9,763,087 appears to relate to "exchanging a cryptographic key between a display device and an input device via electrostatic communication are disclosed. In one embodiment, an interactive communication device includes one or more electrodes and a radio transceiver. The one or more electrodes may be excited to capacitively couple with one or more electrodes of a proximate communication device so as to capacitively send a cryptographic key from the interactive communication device to the proximate communication device. The radio transceiver may be configured to communicate with a radio transceiver of the proximate communication device via a radio channel. The interactive communication device may be configured to subsequently exchange encrypted communications with the proximate communication device over the radio channel. The encrypted communications may be encrypted using the cryptographic key."

US Published patent application no. 2011/0135092 appears to relate "to a method and devices for protecting a reading device (1) for card-shaped data carriers (2) against unauthorised evaluation or copying of magnetically encoded data detected in the reading device (1) for card-shaped data carriers (2). To this end, an electromagnetic noise field (18) is generated by means of a noise field coil (17). The use or disposition of the at least one noise field coil (17) is such that the authorised magnetic field reading head (10) is also affected by the noise field (18) of the noise field coil (17) when the magnetically encoded data of a card-shaped data carrier (2) is being read. An output or sum signal of the authorised magnetic field reading head (10) generated from the wanted signal of a card-shaped data carrier (2) and from the effects of the noise field (18) is detected. The effect of the noise field (18) of the noise field coil (17) in the output or sum signal of the authorised magnetic field reading head (10) is then compensated or filtered out or the wanted signal is selectively filtered out of the output or sum signal of the authorised magnetic field reading head (10)."

US Published Patent Application no. 2007/0293142 appears to disclose "A method for secured communication between a transmitter (10) and a receiver (1) in which a range of power levels transmitted by the transmitter (10) a range of frequencies inside which the transmission will occur, (10) are known or detectable by the receiver (1), the method including transmission by the receiver (1) of a power supply signal for the transmitter characterized in that the receiver (I) transmits for at least the whole duration of the transmission, a noise signal which buries the transmission signal, the receiver (1) subtracts from the received signal, the noise signal in order to obtain a useful signal. The invention also includes a receiving device operating according to the method."

U.S. Published Patent Application no. 20070118188 appears to disclose "A method and system for enabling secure communications between an implantable medical device (ID) and an external device (ED) over a telemetry channel. A telemetry interlock may be implemented which limits any communications between the ED and the ID over the telemetry channel, where the telemetry interlock is released when the ED transmits an enable command to the ID via a short-range communications channel requiring physical proximity to the ID. As either an alternative or addition to the telemetry interlock, a data communications session between the ID and ED over the telemetry channel may be allowed to occur only after the ID and ED have been cryptographically authenticated to one other."

U.S. Published Patent Application no. 20140185805 appears to disclose "Methods and systems for securely exchanging cipher keys between an implantable device and an external device . . . An example method includes: receiving an authorization request from the external device, wherein the authorization request is a request to receive a first cipher key of a cipher key transfer; receiving an indication that a magnet is detected relative to the implantable device, wherein the indication signifies a secure environment for communication between the implantable device and the external device; and after receiving the authorization request and the indication of a detected magnet, generating a first cipher key transmittal instruction, wherein the first cipher key transmittal instruction instructs the first cipher key to be transmitted to the external device by the implantable device."

Additional background art includes US Published Patent Application no. 20110171905, U.S. Pat. Nos. 7,155,290, 9,401,894, 8,331,563, US Published Patent Application no. 20170161449, International Published Patent Application No. WO1999038272, and US Published Patent Application No. 20120174187.

SUMMARY OF THE INVENTION

According to an aspect of some embodiments of the invention, there is provided a method of secure communication between an implanted device and an external device including: inducing an induced current in an implanted device by a nearby external device; modulating a load on the induced current by the implanted device to transmit an encryption key; Generating noise by the nearby external device configured to obscure the modulated load Adding by the nearby external device of the noise to the induced current simultaneous to the modulating; encrypting data by the implanted device using the encryption key to produce an encrypted signal; and transmitting of the encrypted signal by the implanted device.

According to some embodiments of the invention, the noise is on a frequency similar to the modulated load.

According to some embodiments of the invention, the noise has a power at least half of a power of the modulated load.

According to some embodiments of the invention, the method further includes: charging a power source of the implanted device with the induced current prior to the modulating.

According to some embodiments of the invention, the charging includes transferring 0.1 Watt hour of energy to the power source.

According to some embodiments of the invention, the charging includes transferring 0.5 Watts of power to the power source.

According to some embodiments of the invention, the inducing is performed wirelessly from a distance of ranging between 0.5 and 30 cm.

According to some embodiments of the invention, the method further includes, transmitting on higher bandwidth channel/after noise has stopped.

According to some embodiments of the invention, the method further includes checking by the implanted device of for the noise and cancelling the modulating when the noise is not detected.

According to some embodiments of the invention, the method further includes: detecting by the external device of the modulating and wherein the adding is in response to the detecting.

According to some embodiments of the invention, the detecting includes detecting a characteristic of the modulating and wherein the noise is configured to conceal the modulating in accordance to the characteristic.

According to an aspect of some embodiments of the invention, there is provided an implanted device including: an inductive energy receiving circuit; a load modulator coupled to the energy receiving circuit for modulating a load on the energy receiving circuit; a transceiver for data communication; a processor configured for generating an encryption key controlling the load modulator for encoding the encryption key onto a current passing through the inductive energy receiving circuit encrypting data using the encryption key to produce an encrypted signal controlling a transceiver to transmit the encrypted signal.

According to some embodiments of the invention, the device further includes: a sensor connected to the inductive energy receiving circuit for sensing a characteristic of noise on the inductive energy receiving circuit and wherein the processor is further configured to receive output of the sensor and determine the noise is fitting to obscure the modulating of the load and for cancelling the encoding of the key onto the current passing through the inductive energy receiving circuit.

According to some embodiments of the invention, the device further includes: a rechargeable power source and a rectifying circuit connecting the power source to the energy receiving circuit for receiving energy from the energy receiving circuit.

According to some embodiments of the invention, the processor is further configured to initiate the encoding of the encryption key only after a receiving a minimum quantity of energy from an external device.

According to some embodiments of the invention, the processor is further configured to initiate the encoding of the encryption key only after a receiving a minimum power from an external device.

According to an aspect of some embodiments of the invention, there is provided a near field energy transfer device including a power transmitter configured for transferring energy wirelessly to a nearby power receiver circuit; a power generator coupled to power the power transmitter;] a noise generator coupled to the power transmitter to introduce a noise onto the energy; a demodulator coupled to the power transmitter to extract a differential loading signal from the energy; and a noise extraction circuit receiving a characteristic of the noise from the noise generator and coupled to the demodulator to clean the noise from the signal based on the characteristic.

According to some embodiments of the invention, the power transmitter includes an inductor and the transferring is via inductive coupling.

According to some embodiments of the invention, the power generator is configured to produce at least 1 Watt.

According to some embodiments of the invention, the device further includes: a processor configured for determining a characteristic of the differential loading signal and adjusting a characteristic of the noise to obscure the differential loading signal.

According to an aspect of some embodiments of the invention, there is provided a system for secure communication between an implanted device and an external device including: an implanted device including an inductive energy receiving circuit, a load modulator for modulating a load on the energy receiving circuit a transceiver for data communication a processor configured for generating an encryption key controlling the load modulator to encode the encryption key onto a current passing through the inductive energy receiving circuit encrypt data using the encryption key to produce an encrypted signal control a transceiver to transmit the encrypted signal a near field external device including a power transmitter configured for inducting a current on the inducting energy receiving circuit a noise generating circuit to generate a noise on the current.

According to some embodiments of the invention, the implanted device further includes: a sensor connected to the inductive energy receiving circuit for sensing a characteristic of noise on the inductive energy receiving circuit and wherein the processor is further configured to receive output of the sensor and determine the noise is fitting to obscure the modulating of the load and for cancelling the encoding of the key onto the current passing through the inductive energy receiving circuit.

According to some embodiments of the invention, the implanted device further includes: a rechargeable power source and a rectifying circuit connecting the power source to the energy receiving circuit for receiving energy from the energy receiving circuit.

According to some embodiments of the invention, the implanted device further wherein the processor is further configured to initiate the encoding of the encryption key only after a receiving a minimum quantity of energy from the external device.

According to some embodiments of the invention, the processor is further configured to initiate the encoding of the encryption key only after a receiving a minimum power from the external device.

According to some embodiments of the invention, the system further includes: a processor connected to the external device and configured for determining a characteristic of the loading and adjusting a characteristic of the noise to obscure the loading signal.

According to an aspect of some embodiments of the invention, there is provided a method of verifying a communication from an external device and an implanted device including: Sending a message from the external device to the implanted device; inducing an induced current in an implanted device by a nearby external device; modulating a load on the induced current by the implanted device to transmit a verification key; Generating noise by the nearby external device configured to obscure the modulated load Adding by the nearby external device of the noise to the induced current simultaneously to the modulating; transmitting of the verification key to from the external device to the implanted device.

According to some embodiments of the invention, the message is command for the implanted device to perform an action further including: the implanted device waiting to perform the action until receiving the verification key from the external device.

According to some embodiments of the invention, the modulating further is to repeat a portion of the message.

According to some embodiments of the invention, the noise is on a frequency similar to the modulated load.

According to some embodiments of the invention, the noise has a power at least half of a power of the modulated load.

According to some embodiments of the invention, the method further includes: charging a power source of the implanted device with the induced current prior to the sending.

According to some embodiments of the invention, the inducing is performed wirelessly from a distance of ranging between 01 and 30 cm.

According to some embodiments of the invention, the method further includes, transmitting on higher bandwidth channel/after noise has stopped.

According to some embodiments of the invention, the method further includes checking by the implanted device of for the noise and cancelling the modulating when the noise is not detected.

According to some embodiments of the invention, the method further includes: detecting by the external device of the modulating and wherein the adding is in response to the detecting.

According to some embodiments of the invention, the detecting includes detecting a characteristic of the modulating and wherein the noise is configured to conceal the modulating in accordance to the characteristic.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

As will be appreciated by one skilled in the art, aspects of the present disclosure may be embodied as a system, method or computer program product. Accordingly, aspects of the present disclosure may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, some embodiments of the present disclosure may take the form of a computer program product embodied in one or more computer readable medium(s) having computer readable program code embodied thereon. Implementation of the method and/or system of some embodiments of the disclosure can involve performing and/or completing selected tasks manually, automatically, or a combination thereof. Moreover, according to actual instrumentation and equipment of some embodiments of methods, systems, and/or computer program products of the present disclosure, several selected tasks could be implemented by hardware, by software or by firmware and/or by a combination thereof, e.g., using an operating system.

For example, hardware for performing selected tasks according to some embodiments of the present disclosure could be implemented as a chip or a circuit. As software, selected tasks according to some embodiments of the present disclosure could be implemented as a plurality of software instructions being executed by a computer using any suitable operating system. In an exemplary embodiment, one or more tasks according to some exemplary embodiments of method and/or system as described herein are performed by a data processor, such as a computing platform for executing a plurality of instructions. Optionally, the data processor includes a volatile memory for storing instructions and/or data and/or a non-volatile storage, for example, a magnetic hard-disk and/or removable media, for storing instructions and/or data. Optionally, a network connection is provided as well. A display and/or a user input device such as a keyboard or mouse are optionally provided as well.

Any combination of one or more computer readable medium(s) may be utilized for some embodiments. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium and/or data used thereby may be transmitted using any appropriate medium, including but not limited to wireless, wireline, optical fiber cable, RF, etc., or any suitable combination of the foregoing.

Computer program code for carrying out operations for some embodiments of the present disclosure may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Some embodiments of the present disclosure may be described below with reference to flowchart illustrations and/or block diagrams of methods, apparatus (systems) and computer program products. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

DESCRIPTION OF SPECIFIC EMBODIMENTS OF THE INVENTION

Figure 1:
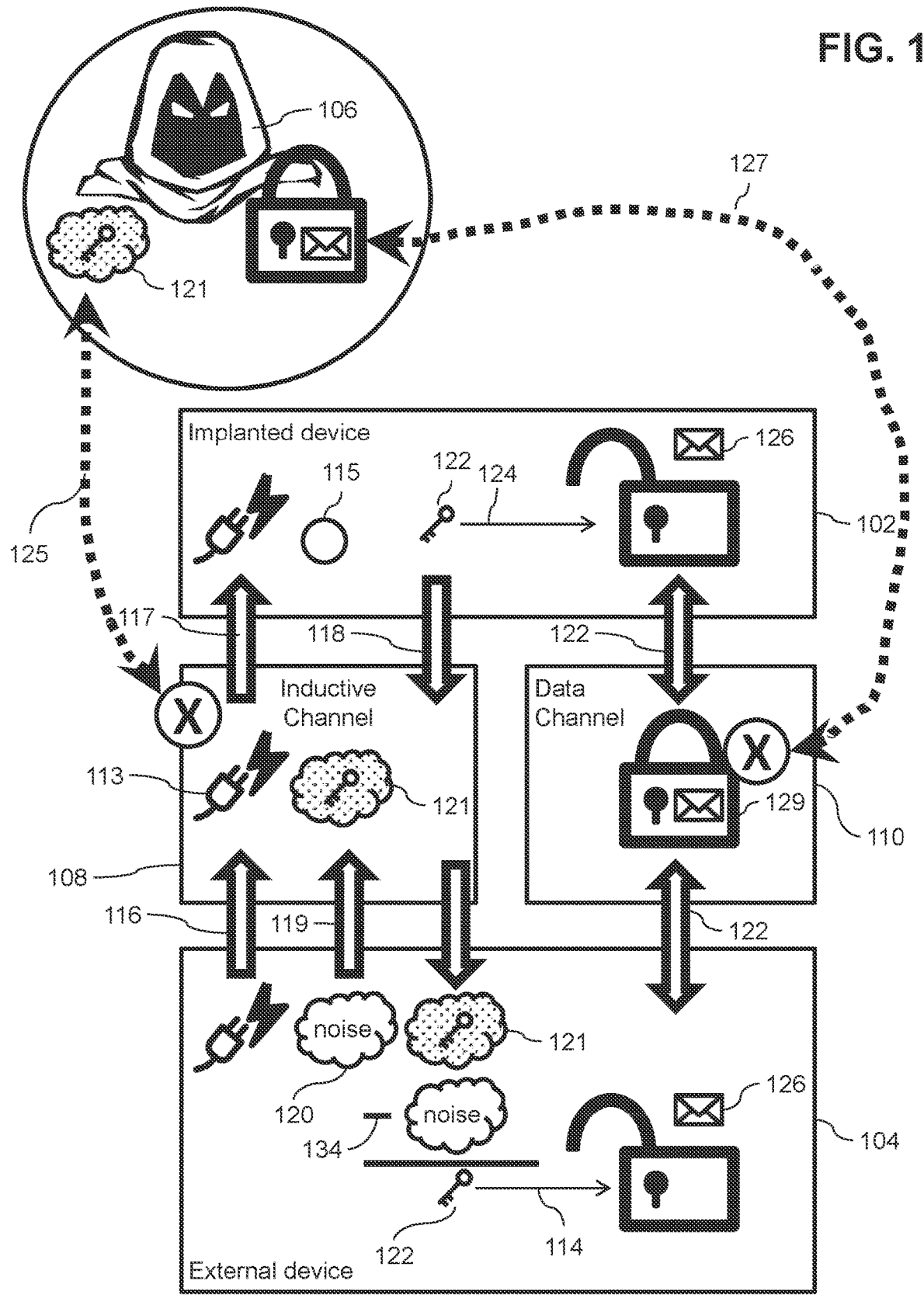
FIG. 1 is a schematic drawing of method of communicating in accordance with an embodiment of the current invention.

The present invention, in some embodiments thereof, relates to a method of securing wireless communication and, more particularly, but not exclusively, to a method of security key transfer with an implanted medical device over a near field communication channel.

Overview

An aspect of some embodiments of the current invention relates to a method for securing a key exchange between an implanted medical device (ID) and an external control device (ED). In some embodiments, an encryption key is transmitted from a transmitter device (e.g. the ID) to a receiver device (e.g. the ED) over a protected channel. Optionally, the receiver device jams communication over the protected channel, while the transmitter device transmits the key to the receiver device over the protected channel. Jamming prevents interception of the security key by an unauthorized (intruder) device. An authorized device optionally extracts the key from a signal received over the jammed channel based on knowledge of the jamming. The key is optionally used for encrypted communication over another non-safe channel.

In some embodiments, the ED may be the receiver device. Optionally the ED supplies power to the ID over an inductance circuit. Additionally or alternatively, the inductance circuit may include a protected data channel. The ED may jam communication by transmitting noise onto the protected inductance circuit and/or the data channel. Optionally the ID transfers the key onto the protected data channel, for example by modulating a load on the inductive circuit. The noise from the ED optionally obscures the security key. Optionally, the content of the noise is known to the ED and/or the ED uses the knowledge of the noise to extract the key from the noisy signal received over the protected channel. Alternatively or additionally, the key may be further obfuscated by using an encoding scheme, for example the scheme may be DC-balanced (e.g. net zero modulation). In some embodiments, the security key will be used to encrypt messages sent over a radio channel. For example, the security key may be used to encrypt data and/or commands being sent over a MedRadio [MICS] channel.

In some embodiments, activating the transmission of the security key from the ID may require actions that would be difficult for an intruder to perform. For example, a powerful transmitter may be required to be located very close to ID. For example, transfer of the security may be initiated only when the ID receives of signal of a sufficient power and/or for a sufficient time and/or over a very short-range channel.

An aspect of some embodiments of the current invention relates to a security protocol for securing wireless communication between an implanted medical device and an external device. In some embodiments, an inductive channel will be secured to prevent eavesdropping by an intruder. Optionally, a security key will be transferred over a protected channel. For example, the security key may be used to secure information transferred over a separate channel. For example, the key may include a symmetric cryptologic key (e.g. a session key). Optionally, there will be different levels of security on the key transfer and/or the key itself (how strong is the key) that are required for different communications.

In some embodiments, for long term reprogramming of the therapeutic activities of the machine the device may require very high security. Short term changes that may be necessary for first aid are optionally available without security barriers. Transferring medical data and/or personal optionally requires medium security while transfer of non-private data (e.g. the battery state of the machine) may require very low security.

In some embodiments, a session key will be communicated over a noisy inductive channel and used for communication over for example the channel on which the new security key will be used may include a MedRadio [MICS] channel). Optionally the protected channel may be used to charge a battery of the ID. In some embodiments a handshake routine may be used to protect the ID from intruders. For example, there may be a key passed to the ID through a different channel and/or a timing and/or a session sequence that is required in order to initiate a security key transfer. Alternatively or additionally, the security key transfer may only be initiated when instructions are supplied over a separate channel. For example, initiation of a key transfer may require a command over a cryptologically secured channel, for example, the channel that will receive be used with new security key, in some cases, for example, when the ID detects an emergency medical situation, certain communications may be allowed with an abbreviated security protocol. Optionally, some functions may be controlled only so long as an inductive device is in communication with the ID. In some embodiments, certain functions may require security clearance including a security key passed over the protected channel In some embodiments, an ID may have various security states and/or have functions that require different security levels for external access. For example, to change life affecting settings of the ID may require high security clearance, for example by use of a fresh security key and/or a key received over a protected channel. Alternatively or additionally, receiving data from the ID may be possible using an older security key. Alternatively or additionally, the ID may have an emergency mode which allows changing of important (and/or life affecting) parameters with a lower security for a limited time. Alternatively or additionally, the security requirements for certain actions may be adjustable by a user having a sufficient security level. Optionally, an ED may have security protection such as a password and/or a biometric identifier to prevent unauthorized access. Alternatively or additionally, some aspects of the ED may require less or no security (for example charging a battery of the ID) while other functions (for example viewing data) may need require medium level security (for example supplying a password) while other functions (for example reprogramming the ID, may require a high(er) security.

An aspect of some embodiments of the current invention relates to an implanted medical device configured to communicate securely with an external device. In some embodiments, an ID may include multiple wireless communication circuits. Optionally, a first circuit is configured for protected communication over a first wireless channel. For example, the first circuit may include an inductive energy receiving circuit and/or a load modulating circuit. Optionally, a second circuit includes a system for communication over a second wireless channel, for example radio frequency transceiver. For example, the second channel may have a higher data rate and/or a longer range than the first channel. In some embodiments, the ID may include a processor configured to generate a cryptographic key and/or transmit the key to an external device over the first circuit. Additionally or alternatively, the processor may be configured to encrypt and/or decrypt communication over the second circuit using the encryption key.

In some embodiments, the implanted medical device includes a rechargeable power supply and/or the first circuit includes a battery charger circuit for supplying power to recharge the power supply. For example, the battery charger unit may harvest, rectify and/or control the power output from the first channel to the rechargeable power supply. Optionally, the rechargeable power supply may supply power for applying non-excitatory electrical signals to heart.

In some embodiments, the ID is paired to an ED including a protected communication circuit for communication over the first protected channel. Optionally the protected communication circuit includes a noise generator configured to generate noise that will prevent interception of the security key over the protected channel. For example, the noise generator may be coupled to the protected communication circuit for example for transmitting the noise over the first channel. Additionally or alternatively, the communication circuit includes a data extraction circuit for subtracting the noise from a received signal to extract the security key. For example, based on the known content of the noise, the extraction circuit may subtract the noise from the received signal. Optionally the ED further includes a power source for supplying power to recharge the power supply of the ID. For example, the power source may include a power generating circuit. Optionally the power generating circuit will include an oscillator. For example, the power source may be connected to the communication circuit such that both power and protected communication are transferred across the first channel. Additionally or alternatively, the ED may include a transceiver for communication over the second channel and/or an encryption circuit for encrypting/decrypting signals over the second channel using the key received over the first channel.

An aspect of some embodiments of the current invention relates to an ED configured for secure communication with an ID. For example, the ED may include a secure channel and/or a radio channel. Optionally, the secure channel may include a very short-range communication medium (for example inductive coupling). The ED is optionally configured to obscure communication on the secure channel and/or to extract data from an obscured signal. For example, the ED may add noise to the secure channel and/or extract data modulated onto the secure channel based on knowledge of the news that was added. For example, the ED may be configured to remove the noise to extract the data. Optionally, the data transmitted over the secure channel may include an encryption key. For example, the ED may be configured to encrypt signals sent and/or received on the radio channel using a key received over the secure channel.

In some embodiments, the ED may include a power source large enough to charge a battery of the ID. In some embodiments, the ED will include security features to prevent misuse of the device. For example, the features may be activated to prevent unauthorized use of the ED for reprograming of the ID. For example, the ED may include a biometric identification system. Optionally, the ED is programmed to change certain parameters of the ED only after positive identification and/or approval of a local use and/or approval of a supervisor (e.g. a doctor and/or a control center). In some embodiments, actions of the ED and/or the ID are logged and sent to a control center. For example, the logs may be checked manually and/or automatically to detect unusual activity and/or potentially dangerous situations.

Embodiments

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings, FIG. 1 illustrates a schematic view of a method of securing communication between an implanted medical device (ID) 102 and an external device (ED) 104 from interception and/or infiltration 125, 125 by an intruder 106. In some embodiments, an ED 104 that is receiving a security key 122 adds 119 noise 120 to the channel 108 over which the key 122 is being transmitted. For example, the ED 104 may use knowledge of the noise 120 that was added 119 in order to clean 134 the signal 121 and recover the key 122. Optionally, an intruder device 106 which does not know the noise 120 content will be prevented from receiving the key 122 over the secure noisy channel 108.

In some embodiments, ID 102 communicates with ED 104 over multiple wireless media, for example a secure medium 108 and a non-secure medium 110. Optionally, the secure medium 108 may be protected from infiltration and/or interception 125. Optionally the secure medium 108 is used by the ID 102 to transfer 118 an encryption key 122. For example, the secure medium 108 may include an inductive channel which is used to transfer 116 energy 113 from the ED 104 to the ID 102. Key 122 may be used to encrypt 124 and/or decrypt 114 a message 126 between the ID 102 and the ED 104. The resulting encrypted message 129 may be transferred 122 over the unprotected channel 110 (for example a MedRadio channel). For example, a message 126 may be encrypted 124 by the ID 102 and/or sent over the unprotected channel 110 from the ID 102 to the ED 104 and/or decrypted 114 by the ED 104. Alternatively or additionally, a message 126 may be encrypted by the ED 104 and/or sent over the unprotected channel 110 from the ED 104 to the ID 102 and/or decrypted by the ID. Optionally Encryption of the encrypted message 129 may protect the message 126 from interception 127 by an intruder 106 and/or use of keyed encryption as identification credentials may foil attempts of the intruder to infiltrate communications between the ID and the ED for example by passing off its messages over the unprotected channel 110 in the name of the ID and/or ED. For example, an infiltration by the intruder 106 may be recognizable because it lacks encryption by the key 122 which is unknown the intruder 106. For example, if the intruder 106 succeeds in intercepting a message 129 over the unprotected channel 110, the message 129 may be encrypted and undecipherable without the key 120 which is unknown to the intruder.

In some embodiments, the ID transfers the encryption key by modulating a 118 a load on the secure channel 108 and/or the coupling between the ID and the ED. For example, the secure channel 108 may include a short-range circuit (for example an inductive charging circuit). In some embodiments communication over the secure channel 108 may be two-way (for example using a simplex and/or duplex protocol). For example, data transfer from the ED to the ID may be protected by the short range of the channel (making it hard to intercept the data without an antenna located very close to the ED) and/or noise generated by the ID. Alternatively or addition data transfer from the ID to the ED may be protected by the short range of the channel and/or by the noise 120 generated by the ED. For example, even if the intruder 106 succeeds in intercepting the message 121 over the secure channel 108, he may be stuck with a noisy signal 121 that he cannot decipher.

In some embodiments, the secure channel 108 may include for example a transcutaneous energy transfer (TET) link (for example including an inductive coupling). For example, an intrusion resistant channel may include a very short-range communication medium (for example inductive coupling). For example, the range of the secure channel may be less than ½ and/or less than ⅕ and/or less than ¹⁄₁₀ and/or less than ¹⁄₂₀ of the range of the non-secure channel. In some embodiments, a secure channel 108 may require high levels of power to transfer a signal. For example, the ID 102 may require transfer of enough power 117 to charge a battery of the ID before sending a signal 118 and/or an encryption key 122 over the secure channel. For example, the power transfer 117 and/or data communication 118 over the secure channel 108 may be in opposite directions (for example from power the ED 104 to the ID 102 and/or transferring a key 122 from the ID 102 to the ED 104. For example, the power transfer 117 may be at a rate ranging between 0.1 to 0.3 Watts and/or 0.3 to 1 Watt and/or 1 Watt to 5 Watts and/or 0.01 to 0.1 Watts and/or 0.001 to 0.01 Watts. Data rate of transmission over the TET channel may range for example between 50 to 200 bits/s and/or 200 to 1 Kbit/s and/or between 1 Kbit/s to 5 Kbit/s and/or between 5 Kbits/s to 20 Kbits/sec. In some embodiments, the ED 104 may charge the ID 102 with between 0.1 to 0.5 Watt hours and/or 0.5 to 1 Watt hour and/or between 0.5 to 10 Watt Hours and/or 0.01 to 0.1 Watt hours and/or 0.001 to 0.01 Watt hours of energy in before a key 122 is transferred and/or in a single session. In some embodiments communication over secure channel 108 may require a large time. For example, the ID 102 may require long contact time before transmitting a key 122 over the secure channel 108. In some embodiments, transferring a message over the secure channel 108 require more than twice the time and/or more than 20 times and/or more than 100 times and/or more than 1000 times the time for transferring the signal over the non-secure channel 110. In some embodiments the length of transmission on the secure channel 110 may be limited, for example to between 1 to 5 cm and/or between 5 to 15 cm and/or between 15 to 100 cm.

In some embodiments, a non-secure second communication channel 110 optionally supports two-way communication. For example, the data transmission rate on the two-way communication channel 110 may range between 1 kbit/s to 100 Kbit/s and/or between 100 Kbit/sec and/or from 100 Kbit/s to 1 Mbit/s and/or between 1 to 5 Mbit/sec and/or between 5 to 25 Mbits/s. Optionally the carrier frequency of the communication channel may range between 402 to 405 and 433 to 435 MHz and/or between 2.4 GHz to 2.5 GHz. In some embodiments, a non-secure medium 110 may be used for two way communication. In some embodiments the length of these transmissions may be limited, for example to between 1 to 3 meters and/or between 3 to 30 m and/or between 30 to 100 meters and/or between 100 to 1000 meters.

In some embodiments, transmission 118 occurs only when noise 120 is being added 119 to the protected channel 108. For example, ID 102 may include a sensor 115 that senses noise 120 on channel 108. Optionally, when sufficient noise in the required frequency is not detected on the channel, the transmission 118 of the key 122 is cancelled. For example, the amplitude of the noise may be between 1 to 5 times the amplitude of the signal and/or between 5 to 20 times the amplitude of the signal and/or between 20 to 100 times the amplitude of the signal.

Figure 2A:
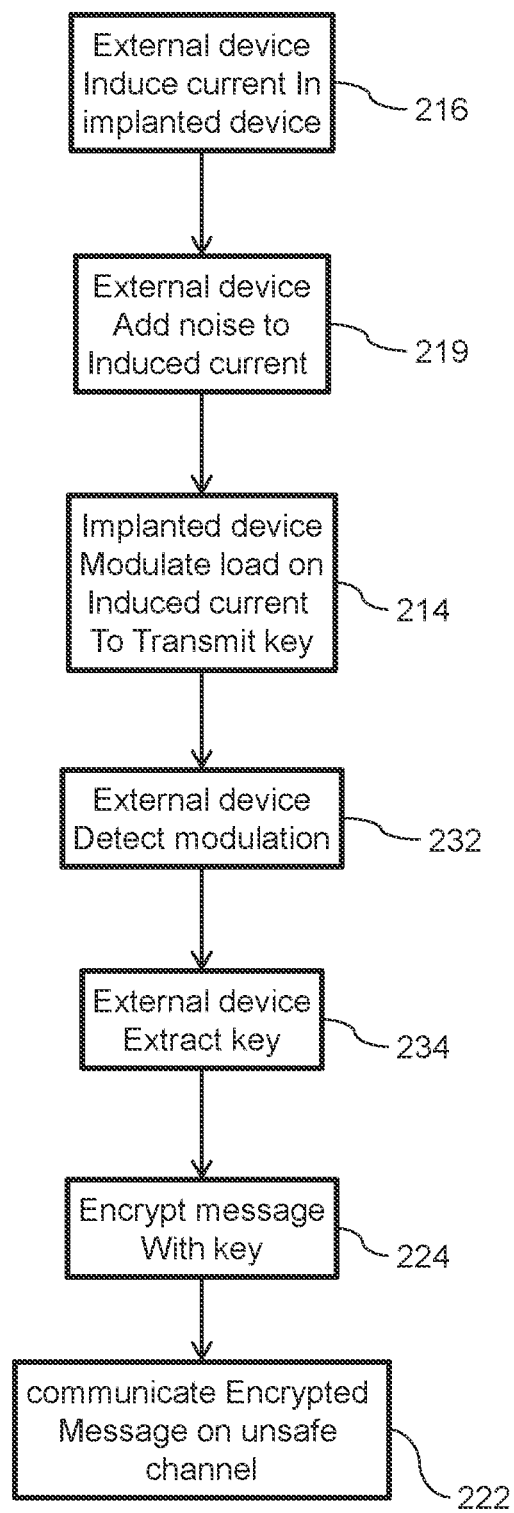
FIGS. 2A and 2B are a flow chart illustrations of methods of communicating in accordance with some embodiments of the current invention.

FIG. 2A, is a flow chart illustration of a method of communicating in accordance with an embodiment of the current invention. In some embodiments, an ED may be used to induce 216 current in a nearby ID. Optionally the ED will also add 219 noise to the induced current, for example, the noise may be configured to conceal data transferred over the induced current. The ID optionally transmits data to the ED by modulating 214 a load on the induced current. In some embodiment, the ED will receive the key from the ID, for example by extracting 234 the modulated message from the noise on the induced current. Optionally, the key is then used for encrypted communication 222 between the ED and the ID for example for encrypting 224 and/or decrypting a message.

In some embodiments, an ED may supply power to an ID. Optionally, power may be supplied by inductive coupling. For example, the ED may induce a current 223 in the ID. The induced current is optionally, used to power the ID and/or to charge a power source (e.g. a battery) of the ID.

In some embodiments, while the ED is inducing 216 current in the ID, the ID may modulate 214 the current and/or encode data onto the induced current. For example, the data may include an encryption key that may be used for encrypted communication 222. For example, the encrypted communication may be over another channel and/or between the ID and the ED. Alternatively or additionally, the key may be used for encrypting communication between the ID and another device.

In some embodiments, add 219 a fixed noise signal to the induced current. Alternatively or additionally, the ED may detect 232 the modulation of the ID and/or add noise tuned to conceal the data modulation. Optionally, the signal from the ID may include a preamble which warns the ED that secret data is coming and/or informs the ED of some characteristics of the modulation. Optionally the ED configures the noise in accordance with the characteristics of the signal, such that the signal is concealed. For example, significant signal characteristics may include the time of transmission, the length of the transmission, the power of the transmission, the frequency of the signal etc. For example, some optional characteristics of the signal are described herein above with respect to FIG. 1.

In some embodiments, the ED may use knowledge of the noise that was added 219 to the induced current for extracting 234 the key. For example, the ED may subtract the noise from the received signal to produce a clean signal from which the key can be read.

In some embodiments, the key transferred 214 over the induced current is for encrypted communication 222. For example, the key may include key for symmetric encryption (e.g. a session key) and/or a key for asymmetric encryption. For example, the key may be used for encryption and/or decryption. Optionally the encryption may be used for communication on the induced current and/or over another channel (for example as described in connection with FIG. 1 herein above). The encrypted communication 222 may include sending data from the ID and/or sending instructions from the ID to the ED. Optionally differing levels of security may be used for different communications, for example as explained in other embodiments described herein.

Figure 2B:
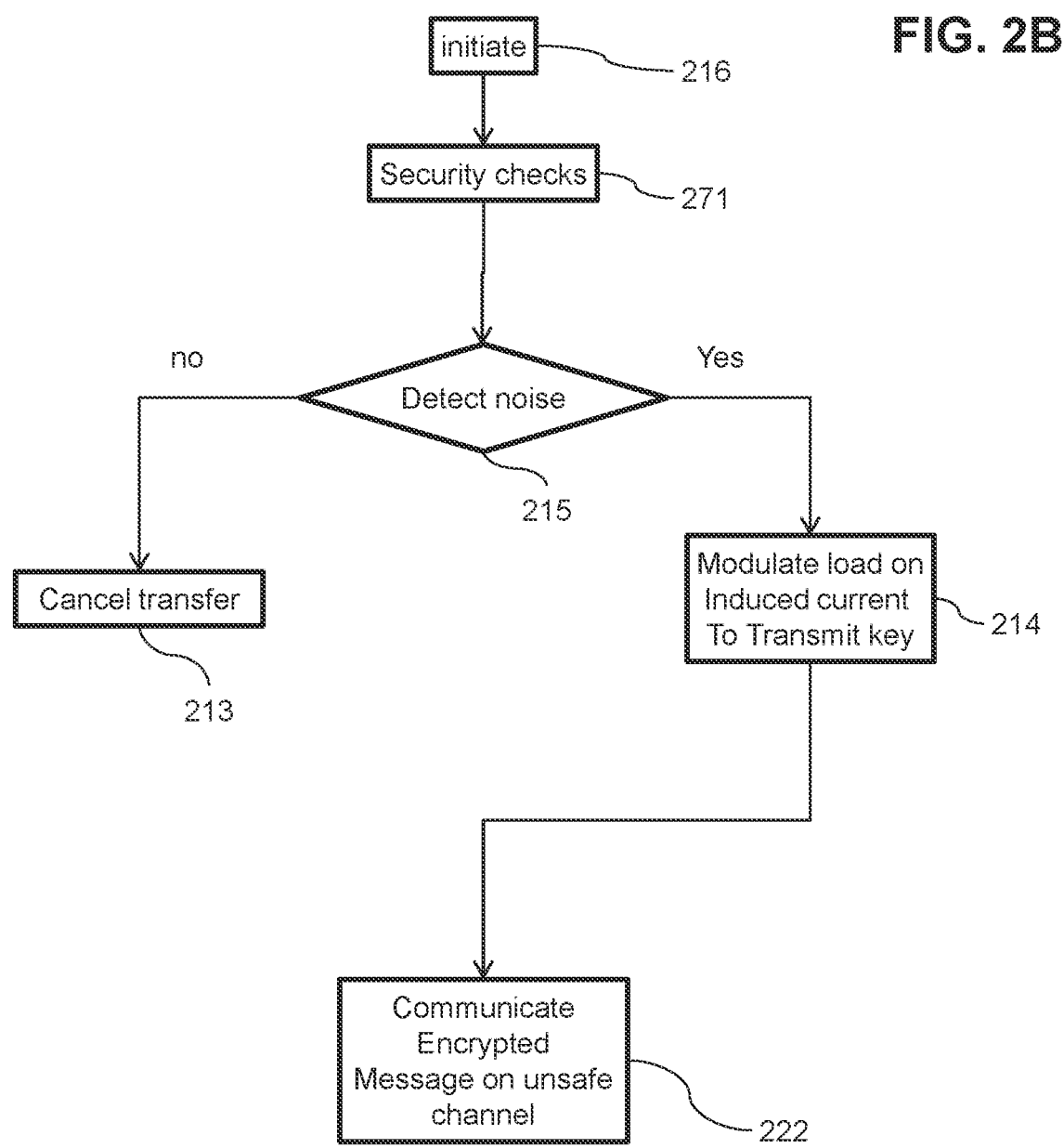

FIG. 2B, is a flow chart illustration of optional further security aspects of a method of communicating in accordance with some embodiments of the current invention. Various embodiments of the current invention may include some, none, or all of the security steps illustrated in FIG. 2B. For example, an ID may include a sensor circuit which senses noise in the induced current and/or the noise. Optionally, when the noise and/or the induced current is detected 215 according to specifications (e.g. having enough power, over enough time, of the proper frequency) the key is transmitted 214 and/or when the noise and/or the current are detected 215 not according to specifications, transfer of the key is cancelled 213.

In some embodiments, an operator initiates 216 a secure session. For example, the operator moves the ED to a position alongside a subject near a location where the ID is implanted. For example, the ED may be held less than 5 cm from the ID and/or between 5 to 10 cm and/or between 10 to 20 cm and/or between 20 to 50 cm between 50 to 200 cm from the ID. A communication link may open automatically as a result of the proximity of the ED to the ID Alternatively or additionally, the operator may activate the ED and/or the operator may initiate charging the ID over a TET link. Alternatively or additionally, the ID may remain active polling a communication channel (without an external initiation). Alternatively or additionally, the ID may include a reed switch which is activated by a magnet in the ED and/or over the TET link.

In some embodiments, the session begins with a security check. For example, the ED transmitting a beacon signal to the ID. Optionally the signal may be a MedRadio signal (e.g. a 402-405 MHz signal). Optionally, the ID is periodically polling for the beacon. Alternatively or additionally, the ED may activate the communication of the ID. Alternatively or additionally, the security check 271 will include a communication between the ED and the ID over the secure channel. For example, the ED 304 may monitor the noise and/or signal over the TET channel and/or instruct the ID 302 to transfer the key when the signal is concealed and/or to cancel the transfer when the signal is not properly concealed. Communication between the ID 302 and ED 304 is optionally over the TET channel and/or over another channel (for example a MedRadio channel).

In some embodiments, when the ID connects to the ED, a key is generated and/or sent to the ED. Alternatively or additionally, the ID may wait for a request for the key and/or for a further security check before sending a key.

In some embodiments, the request for the new key will be transmitted over another channel (for example the unprotected channel, optionally using encryption, for example using a previously agree key). Alternatively or additionally, a security check 271 may include some action on the secure channel, for example a certain time of activation and/or a certain quantity of energy transferred and/or a certain power transferred and/or detection of the noise. Alternatively or additionally, the security check may require a device to relay information on one channel that was available only through communication on the other channel, for example a verification code and/or a message sequence number and/or a time of a communication etc.

Figure 3:
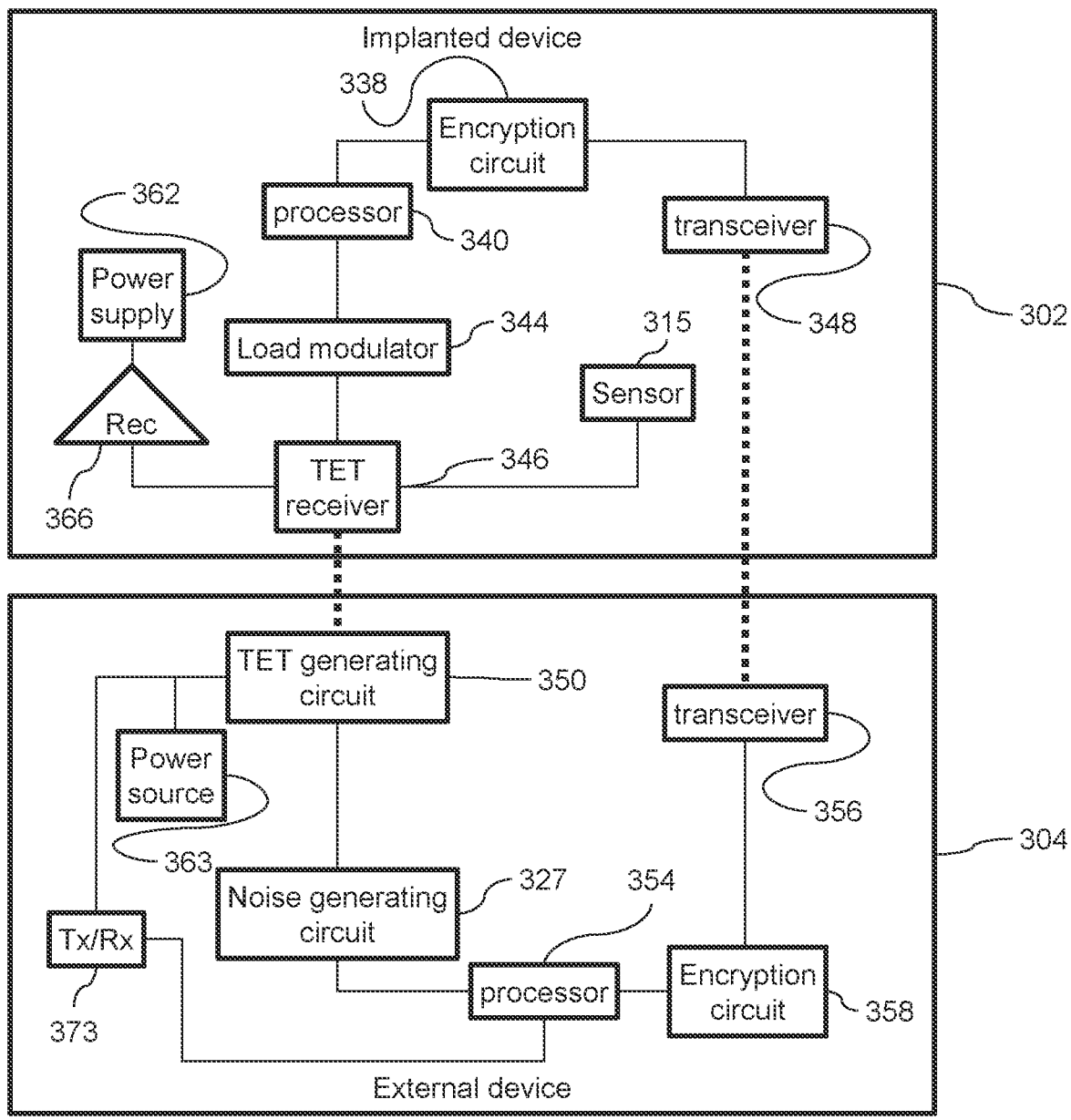
FIG. 3 is a block diagram of system for communicating in accordance with an embodiment of the current invention.

FIG. 3 is a block diagram of system for communicating in accordance with an embodiment of the current invention. In some embodiments, a system includes an ID 302 and/or an ED 304. In some embodiments, the ED 304 includes a demodulator 373 (which may also include a modulator) and/or a noise generating circuit 327 coupled to a power transmitter, for example TET generating circuit 350. For example, while the demodulator 373 is receiving a signal, the noise generating circuit 327 optionally generates noise that obscures the signal. A processor 354 optionally uses knowledge about the noise to extract the noise and recover received signal. Additionally or alternatively, the processor 354 may use information about the signal to adjust the noise to better conceal the signal from intruders. Optionally, the ID 302 includes a sensor 315 for sensing whether there is enough noise on the TET channel to conceal the signal. For example, sensor 315 may be connected to the TET receiver. Optionally when there is enough noise, the ID 302 will transmit the encryption key; when there is not enough noise, the ID 302 will cancel transmission of the key. For example, the ID 302 could contain a narrowband power sensor focused on the signal frequency and a wideband power sensor. Transmission may only occur when the measurement of the wideband sensor is sufficiently greater than that of the narrowband for example, when the broadband is between 2 to 5 times as strong and/or between 5 to 20 times as strong and/or between 20 to 100 times as strong. In some embodiments, the ID 302 could measure power at a number of points with a short delay between them and ensure that the spread is greater than or equal to a predefined range value.

In some embodiments, the ID 302 includes a TET receiving circuit 346 and/or a load modulator 344. Optionally, the TET receiving circuit includes an energy receiving circuit. For example, the energy receiving circuit may be configured for receiving inductive energy and/or include a coil for harvesting inducted energy. Optionally the energy receiving circuit may supply energy to the ID 302. For example, the ID 302 may include a rectifying circuit 366 that extracts energy for the TET receiver 346. For example, energy may be supplied to a power supply 362 (for example a rechargeable battery) of the ID 302.

In some embodiments, the load modulator 344 may include a retromodulation circuit and/or protocol for modulating signals onto the TET channel. Optionally a processor 340 and/or an encryption circuit 338 encode messages and/or encryption keys. Processor 340 and/or circuit 338 may be connected to modulator 344 and/or communication with modulator 344 for transmission of the messages and/or keys over the TET channel to the ED 304. Optionally, encryption circuit 338 may be included in processor 340, for example as software and/or hardware.

In some embodiments, the ID 302 includes a transceiver 348 for wireless communication. Optionally, transceiver 348 may communicate of a radio channel (for example MedRadio). For example, transceiver 348 may be used to communication with ED 304.

In some embodiments, an ED 304 includes a TET generating circuit 350. For example, the TET generating circuit 350. For example, circuit 350 may include a coil for producing a magnetic signal. For example, the magnetic signal may induce a current in the TET receiver 346. Optionally, a power source 363 supplies power to circuit 350. For example, the power is wireless transferred to the ID 302. Optionally, a modulator/demodulator 373 is also in communication with the TET generating circuit 350. For example, communication of signals may be sent to the ID 302 of the TET circuit. Optionally, when communicating signals to the ID 302, the ED 304 adjusts (e.g. reduces) noise generation to facilitate reception by the ID 304. In some embodiments, the ID may include a noise making circuit for adding noise to the TET channel when the ID 302 is receiving a signal and/or a noise subtracting circuit for subtracting the noise from the received signal.

In some embodiments, the noise generating circuit 327 may activated in response to an incoming signal from the ID 302. For example, the noise generating circuit 327 may be activated when any signal is detected from the ID 502. Alternatively or additionally, the noise generating circuit 327 is activated in response to a particular message from the ID 302. For example, the noise generating circuit 327 may be activated automatically when the ID 302 starts to transmit secret information (e.g. a security key). Alternatively or additionally, the noise generating circuit 327 may be activated in response to a request from the ID 302 and/or in response to a message from the ID 302 that it will be sending a secret data. Optionally the request and/or message may be sent over the TET channel and/or received by modulator/demodulator 373. Alternatively or additionally, the request and/or message may be sent over another channel (for example a MedRadio channel) and/or received by another receiver (for example a radio transceiver 356 of the ED 304).

In some embodiments, the ED 304 includes a transceiver 356 working on a channel separate from the TET channel. For example, transceiver 356 may work on a MedRadio channel. For example, transceiver 356 may communication with the ID 304. Optionally an encryption circuit 358 may encrypt and/or decrypt signals of the TET channel and/or on another channel (in some embodiments, encryption circuit 358 may be embodied in the form of a software algorithm running, e.g., in processor 354). Alternatively or additionally, ED 304 may communicate with a network and/or with another device (for example a personal computer, a local network, a cellular network, a cellular device etc.) In some embodiments, a processor 354 may be connected to and/or control and/or or coordinate various parts of the ED 304.

In some embodiments, the ID 302 and/or ED 304 may include a security warning system. For example, a warning may be issued when a suspicious event occurs. For example, when a device (302, 304) is taken far away from its current location and/or given unusual commands and/or tampered with. Optionally, the warning will be issued by a visible and/or audible signal. Alternatively or additionally, the warning will be transmitted over a radio link and/or a network. For example, the warning may be sent to a cellular device of a user. Alternatively or additionally, the warning will be sent to a supervisory individual and/or organization. In some embodiment, a security level of the ED will change dependent on location and/or time and/or conditions (for example requiring more user identification in order to operate in some conditions than others).

Figure 4:
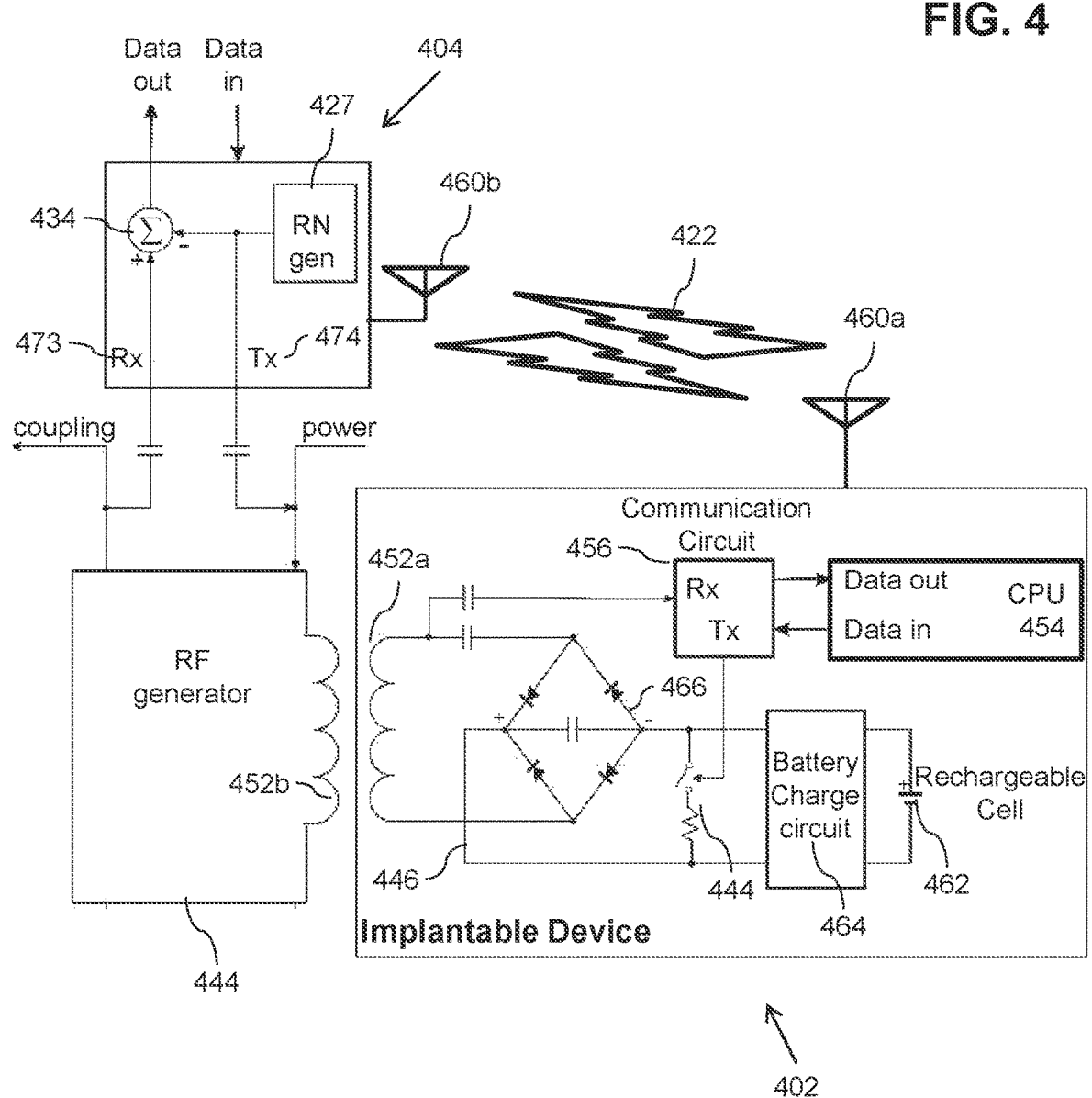
FIG. 4 is a circuit diagram of system for communicating in accordance with an embodiment of the current invention.

FIG. 4 is a circuit diagram of system for communicating in accordance with an embodiment of the current invention. In some embodiments, coil 452b of an ED 404 receives power from a power generator. The power is optionally transferred over a TET link to the IMD 402. Optionally, the ED 404 includes a noise generating circuit 427 and/or modulator 474 for producing noise on the TET link. In some embodiments, the ID 402 includes a communication circuit 456 for modulating a signal onto the TET link. Optionally, the signal may be modulated as a series of changes in load of the coil 452a. For example, a variable resistance circuit 444 and/or switch may be connected to coil 452a and associated circuitry 446 and/or an associated rectifier 466. A demodulator circuit 473 of the ED 404 optionally detects signals on the TET link. A signal cleaning circuit 434 optionally cleans the noise from the signal detected by demodulating circuit 473 and/or outputs the signal that was modulated by communication circuit 456. For example, circuit 434 may receive a record of noise produced by circuit 427 and subtracts the effective noise from the output of demodulator 473.

In some embodiments, the TET link may transfer power and/or data inductively to an inductance coil 452*a* of an IMD 402. Optionally, coil 452*a* is connected via rectifying circuit 466 (for example a full bridge rectifier as depicted in FIG. 4) to a charge control circuit 464 and/or a rechargeable power source 462.

Module 456 is optionally configured for sending and/or receiving signals over a radio transceiver 460*a*. For example, module 456 may be configured for decryption and/or encryption of signals over a two-way radio channel 422. Optionally, transceiver 460*a* includes a dedicated antenna. Alternatively or additionally, transceiver 460*a* uses coil 452*a* as a radio antenna. Communication is optionally controlled by a controller 454. Optionally, coil 452*a* may be connected to a signal receiver circuit which demodulates an incoming signal over the TET link. For example, circuit may be connected to coil 452*a* via a tuned capacitor and/or band pass filter.

In some embodiments, an ED 404 includes a transceiver 460*b* for communicating of radio channel 422 with IMD 402. Optionally, ED 404 includes a processor 454. For example, processor 454 may be configured for encoding and/or decoding and/or for generating of keys for encryption/decryption. Processor 454 optionally generates an encryption key and transmits it over the TET link via circuit 456 to the ED 402. Optionally communication over the radio channel 422 uses the encryption key.

Figure 5:
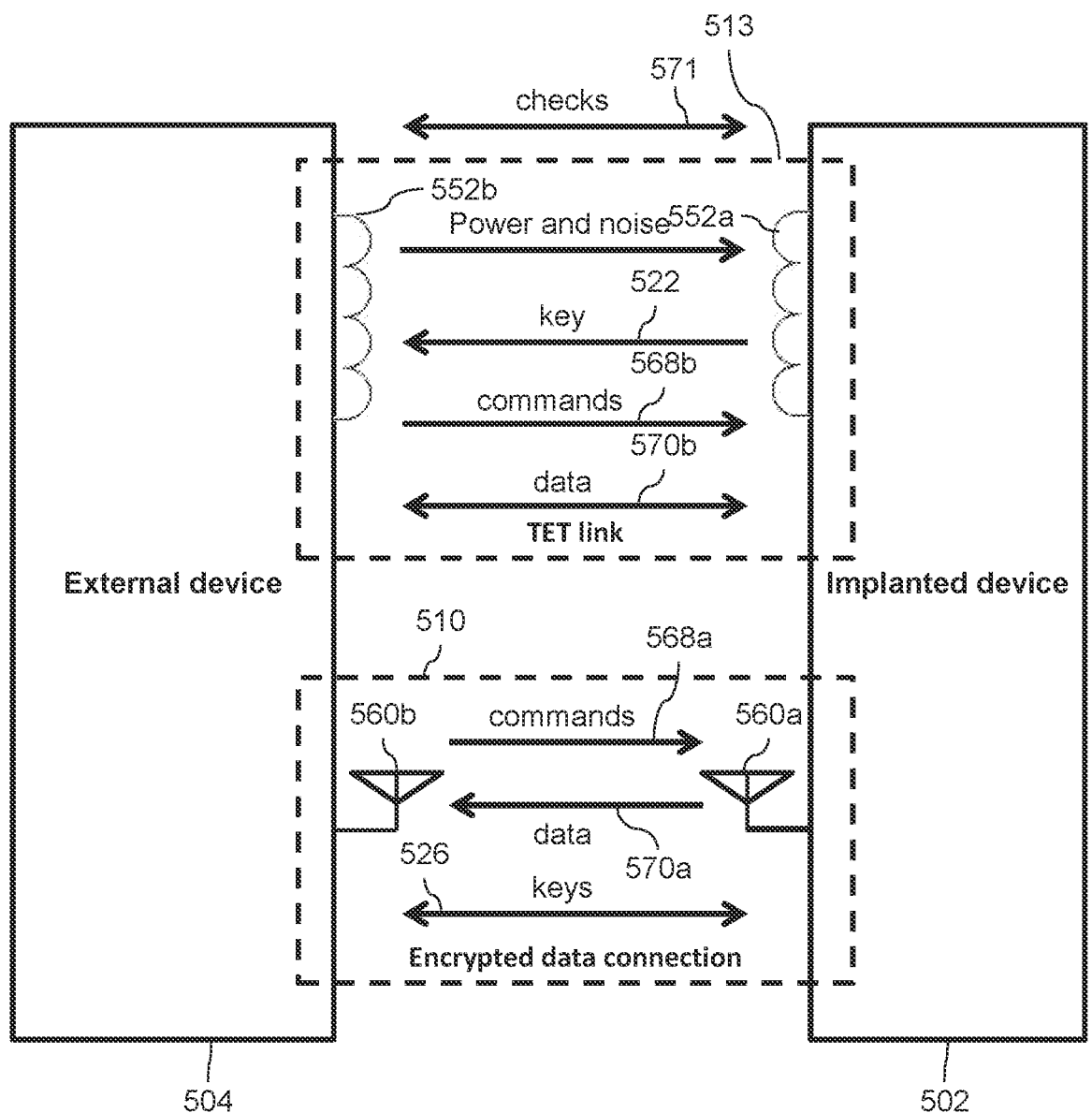
FIG. 5 is a block diagram illustrating signal flow in accordance with an embodiment of the current invention.

FIG. 5 is a schematic diagram illustrating signal flow and/or security protocols in accordance with an embodiment of the current invention. Various contents of communications and/or security states may be protected by various security protocols for example in accordance with a sensitivity and/or urgency of the communication.

In some embodiments, a communication channel over a short range TET link 513 is used for transferring 522 an encryption key for encryption of a message. The message may include, for example, further encryption keys 526 and/or a command 568*a* and/or data 570*a* transmitted between an ED 504 and an IMD 502 over a communication channel 510. Alternatively or additionally, the TET link 513 may be used for verification 571 of a message sent from the ED 504 to the IMD 502 and/or for sending a command 568*b* and/or data 570*b* between the ID 302 and the ED 304 either from the ED 504 to the IMD 502 and/or from the ID 302 to the ED 304. In some embodiment, communication over a TET is further protected by an authentication protocol.

In some embodiments, a TET link 513 may be used for verification 571 of a message over the channel 510. For example, when ED 504 gives a highly sensitive command (for example a command to change a treatment parameter of the IMD 502) the IMD 502 may require verification 571 over the TET link 513. For example, verification 571 may include a simple statement verifying that the ED 504 sent a command 568*a* over the channel 510. Alternatively or additionally, the verification message may include a password and/or a time stamp and/or a packet ID number that identifies the message from the link 510.

In some embodiments, a session on the link 510 may have multiple security keys that change from time to time and/or according to instructions passed over the TET link 513 and/or according to instruction passed over an encrypted conversation in the channel 510 and/or according to stored data shared between the IMD 502 and the ED 504. Switching of session keys from time to time may make it harder to break the encryption of the channel 510 by statistical means.

In some embodiments, the IMD 502 may periodically send a list of settings and/or treatment parameters to the ED 504. For example, the data may be checked periodically to make sure that no settings were inadvertently and/or maliciously mis-set.

In some embodiments, a limited range of changes in treatment settings of the IMD 502 may be permitted with a relatively low level of security while other changes may require higher security. For example, the IMD 504 may include a read only and/or a read write memory with stored ranges of settings that are allowed with relatively low security. Alternatively or additionally, relatively small changes in parameters may be allowed with lower security than a larger change.

In some embodiments the TET link 513 may include an inductive channel. For example, a signal and/or energy may be sent from an inductor (for example a coil 552*b*) of the ED 504 to an inductor (for example a coil 552*a*) of the IMD 502. In some embodiments, the channel 510 may include a radio channel. For example, radio signals may be sent back and forth between a transceiver 560*a* of the IMD 504 and a transceiver 560*b* of the ED 504. Optionally, transceiver 560*a* may include a dedicated antenna. Alternatively or additionally, transceiver 560*a* may use coil 552*a* as an antenna.

In some embodiments, an IMD may have various security states. For example, the IMD may recognize a state in which there is an increased risk of malicious attack. For example, there may be an increased risk of malicious attack when the device (and/or the person to which the device is implanted) is in an unsecured location and/or when the person in whom the device is implanted is asleep and/or at night.

Optionally, the IMD 504 may include positioning indicator and/or a sensor to determine a state of the user. For example, in a state with increased risk of attack, a device may not allow certain sensitive communications. Alternatively or additionally, in a state where there is increased risk the IMD 502 may require increased security protocols and/or verification over a normal mode.

In some embodiments an IMD 502 may have an emergency mode. For example, when an IMD 502 detects a symptom of a dangerous health condition the IMD 502 may enter an emergency mode and/or an authorized medical authority may be empowered to switch the device to the emergency mode. For example, in the emergency mode, the IMD 502 may take action to protect the user (for example to increase blood flow and/or stabilize cardiac activity). Alternatively or additionally, in the emergency mode, the IMD 502 may lower security and/or allow emergency and/or medical personnel to make short term changes in the functioning of the IMD 502. Optionally, the IMD 502 may have a memory (read only and/or read write) that stores certain actions that are allowed in one or more emergency situations with reduced security. Optionally the IMD 102 may have a computer readable memory (for example a RW and/or RO memory) that stores the restore and/or default and/or current parameter values that can be restored after the temporary parameters expire and/or the emergency situation changes. Optionally, the IMD 102 may include a real time clock. For example, the clock may be used to determine when a parameter value has expired and/or should be changed. In some embodiments there may be one or more code and/or special field (e.g. a strong magnetic field and/or with certain polarization or dynamic property such as angle) that will modify the ID functionality, for example, one or more of shut down the ID, cause the ID to inhibit therapy, cause the ID to move to a limited operation mode (e.g., a "safe" mode), optionally on a temporary basis (e.g., with a time limit, after which a different operational mode occurs).

In some embodiments, different commands and/or actions may require different levels of security. For example, a command to change a setting of the IMD 502 that may in a short-term cause significant harm and/or danger to the user may require the highest level of security. For example, a long-term change is a setting of the IMD 502 that could cause danger and/or harm to the user may require a high level of security. For example, a short-term change in a setting of the IMD 502 and/or a change that is unlikely to cause significant harm or danger to a user may require a medium level of security. For example, communication of health and/or sensitive data may require a medium level of security. For example, communication of non-sensitive data (for example a battery level) may require low level of security.

In some embodiments, a different level of security may require a different security protocol. For example, a message at the highest security may require individual verification over the TET channel 513. Alternatively or additionally, a message at the highest security may be allowed on a channel 510 when the security key is fresh (for example when the security key was fixed based on a communication over the TET channel within the last minute and/or within the last 10 minutes and/or within the last half hour and/or within the last six hours). Optionally, a message at a high level of security may be accepted based only on the security of the channel 510 and/or with an older security key than the highest security level, for example when the security key was fixed based on a communication over the TET channel within the within the last 10 minutes and/or within the last half hour and/or within the last six hours and/or within the last day and/or if the device has been in a safe location since the last security key refresh. Optionally, for medium and/or low-level security an older key may be acceptable and/or even a non-secured communication link may be used.

In some embodiments, verification and/or key transfer on the TET channel may be secured by authentication. Optionally, authentication of TET communications may be required for high level security actions. For example, authentication may include requiring the TET channel to transfer a large amount of power and/or energy and/or to transfer power over a long time (something that may be particularly difficult for a malicious intruder). Alternatively or additionally, authentication may require use of a code or another verification of the identity of the ED 504. Alternatively or additionally, authentication may include security verification over another channel (e.g. channel 510) before accepting a security key over the TET. In some embodiments, the verification 571 may include sending a parameter value over the TET 513 link. In some embodiments, verification will include repeating a parameter value sent over channel 510. Alternatively or additionally, a command may be given over channel 510 to change a parameter value and the new value may be given over the TET link 513. Alternatively or additionally, a value may be given over channel 510 and a message defining which parameter to change may be sent over the TET link 513. In some embodiment, an authentication may include a requirement of an operator identification. For example, an ED 504 may include a bio-metric device and/or an input device for identifying an operator. In some embodiments, an IMD 502 will allow a temporary change of state and/or therapeutic parameter prior to verification. For example, when verification is received in time, the new state may be preserved. Optionally, when verification is not received in a predetermined time, the IMD 502 may revert back to a previous state and/or parameter. In some embodiments, when a sensitive command is issued from the ED 504 to the ID 302, the ID 502 will send a verification code over the TET link to the ID 504. Optionally, the ID 502 will then only implement the command when the ED 504 repeats the verification code and/or the command to the ID 502.

Figure 6:
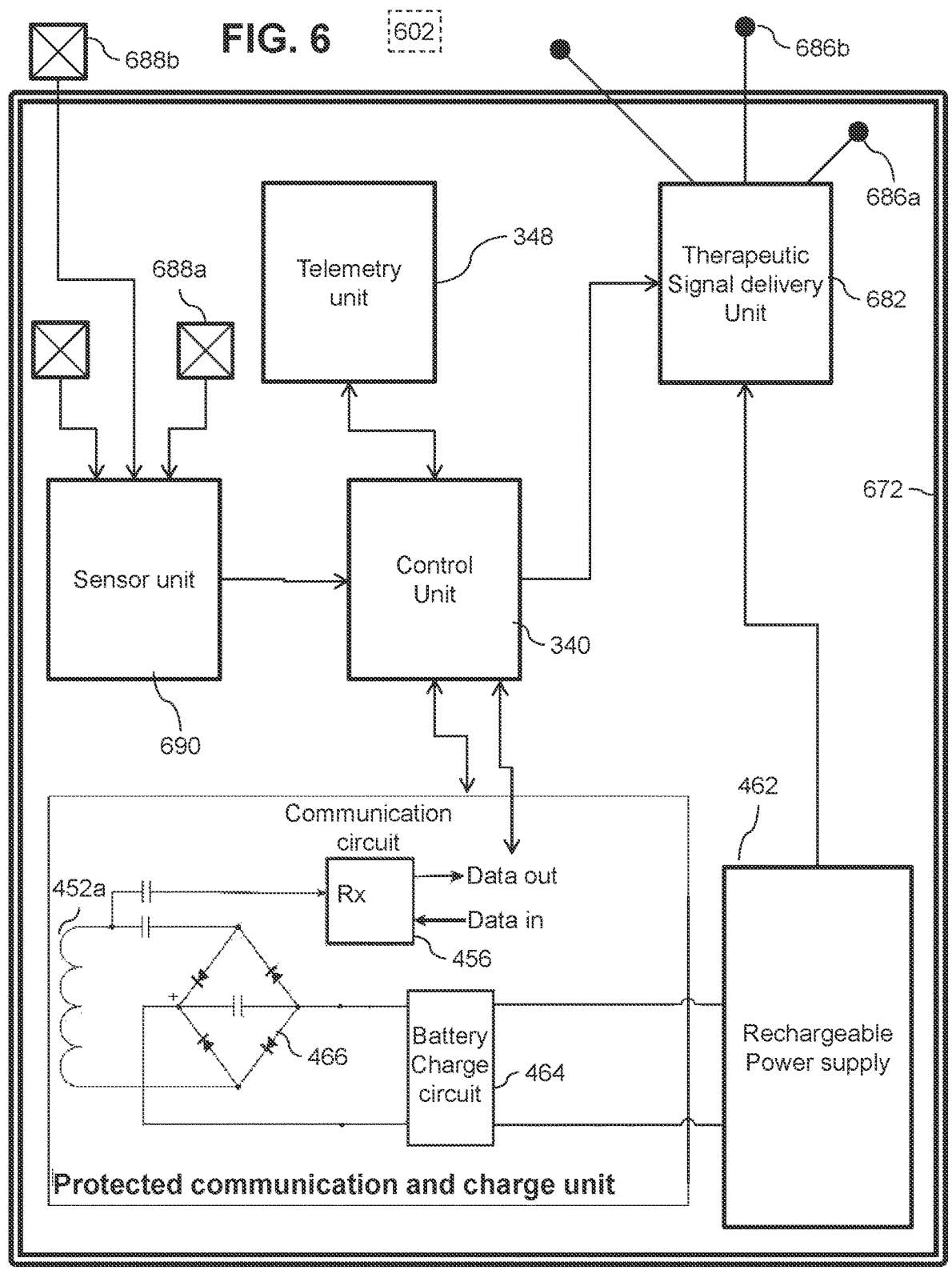
FIG. 6 is a block diagram of an implanted medical device in accordance with an embodiment of the current invention.

FIG. 6 is a block diagram of an IMD 602 in accordance with an embodiment of the current invention. In some embodiments, an IMD 602 includes a therapeutic unit 682 and/or a sensor unit 690. For example, a therapeutic unit may include actuators 686a 686b that apply therapies to tissue. For example, the sensor unit 690 may include sensors 688a 688b which sense a condition of a user of the device.

In some embodiments an IMD 602 may be encased in a protective cover 672 (for example cover 672 may be water proof, biocompatible, protect the user from the internal parts of the IMD and/or protect the user from electric shock and/or to protect internal parts of the IMD 602 from body fluids and/or to protect the IMD from physical damage for example knocks). Optionally one or more sensors (for example sensor 688a) are inside cover 672. For example, sensor 688a may sense a magnetic field. Alternatively or additionally, a sensor that extends outside of cover 672 (for example sensor 688b). For example, sensor 688b may include an electrode, pressure transducer, a thermocouple and/or a flow meter.

In some embodiments, one or more actuators (for example actuator 686a) are inside cover 672. For example, an actuator 688a may produce a magnetic field. Alternatively or additionally, an actuator that extends outside of cover 672 (for example actuator 686b). For example, actuator 686b may include an electrode, an ultrasound transducer and/or a heating element. In some embodiments a single element may serve both as a sensor and an actuator. For example, an electrode may be used to collect information about electrical signal inside the user and/or also apply an electrical signal. For example, IMD may include a pacemaker and/or an implantable cardiac defibrillator (ICD) and/or a cardiac contractility modulation (CCM) device. For example, the device may apply pacing signals and/or non excitory signals at various periods of the cardiac cycle.

It is expected that during the life of a patent maturing from this application many relevant communication, sensing and/or therapeutic technologies will be developed and the scope of the terms channel, sensor, noise, signal, actuator are intended to include all such new technologies a priori.

As used herein the term "about" refers to ±5%

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference.

In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

What is claimed is:

1. A method of secure communication between an implanted device and an external device comprising:
   inducing an induced current in an implanted device by a nearby external device;
   modulating a load on said induced current by said implanted device to transmit an encryption key;
   generating noise by said nearby external device to obscure said key transmission on said modulated load;
   adding by said nearby external device of said noise to said induced current simultaneous to said modulating;
   encrypting data by said implanted device using said encryption key to produce an encrypted signal; and
   transmitting of said encrypted signal by the implanted device, wherein said method comprises:
   checking by said implanted device for said noise; and
   cancelling said modulating when said noise is not detected or is determined to not be fitting to obscure said key transmission.

2. The method of claim 1, wherein said noise is on a frequency similar to said modulated load.

3. The method of claim 1, wherein said noise has a power at least half of a power of said modulated load.

4. The method of claim 1, further comprising:
   charging a power source of said implanted device with said induced current prior to said modulating.

5. The method of claim 4, wherein said charging includes transferring at least 0.1 Watt hour of energy to said power source.

6. The method of claim 4, wherein said charging includes transferring at least 0.2 Watts of power to said power source.

7. The method of claim 1, wherein said inducing is performed wirelessly from a distance of ranging between 0.5 and 30 cm.

8. The method of claim 1, further comprising, transmitting on higher bandwidth channel/after noise has stopped.

9. The method of claim 1, further comprising cancelling said modulating when said noise is not detected.

10. The method of claim 1, further comprising:
    detecting by said external device of said modulating; and
    wherein said adding is in response to said detecting.

11. The method of claim 10, wherein said detecting includes detecting a characteristic of said modulating and wherein said noise is configured to conceal said modulating in accordance to said characteristic.

12. The method of claim 1, wherein said transmitting of said encrypted signal by the implantable device comprises transmitting over an unprotected data channel.

13. The method of claim 1 and further comprising sending a message from the external device to the implanted device.

14. An implantable device comprising:
    an inductive energy receiving circuit;
    a load modulator coupled to said energy receiving circuit for modulating a load on said energy receiving circuit;
    a transceiver for data communication;
    a processor configured for:
      generating an encryption key;
      controlling said load modulator for encoding said encryption key onto a current passing through said inductive energy receiving circuit;
      encrypting data using said encryption key to produce an encrypted signal;
      controlling a transceiver to transmit said encrypted signal; and
      checking by said implanted device for noise suitable to obscure said modulation of said key on said load; and
      cancelling said modulating when said noise is not detected or is determined to be not fitting to obscure said modulation of said key on said load.

15. The device of claim 14, further comprising:
    a sensor connected to said inductive energy receiving circuit for sensing a characteristic of noise on said inductive energy receiving circuit and wherein said processor is further configured to receive output of said sensor and use said output for said determining if said noise is fitting to obscure said modulating of said key on said load and for cancelling said modulation by cancelling encoding of said key onto the current passing through the inductive energy receiving circuit.

16. The device of claim 14, further comprising:
a rechargeable power source; and
a rectifying circuit connecting said power source to said energy receiving circuit for receiving energy from said energy receiving circuit.

17. The device of claim 14, further wherein said processor is further configured to initiate said encoding of said encryption key only after a receiving a minimum power from an external device.

18. A system for secure communication between an implantable device and an external device comprising:
an implantable device according to claim 14; and
a near field external device including:
a power transmitter configured for inducting a current on said energy receiving circuit; and
a noise generating circuit to generate a noise on said current.

19. The system of claim 18, wherein said controlling a transceiver to transmit said encrypted signal comprises controlling to transmit over an unprotected data channel.

20. The system of claim 18, wherein said implantable device further comprises:
a sensor connected to said inductive energy receiving circuit for sensing a characteristic of noise on said inductive energy receiving circuit and wherein said processor is further configured to receive output of said sensor and use said output for said determining if said noise is fitting to obscure said modulating of said load and for cancelling said modulation by cancelling encoding of said key onto the current passing through the inductive energy receiving circuit.

21. A method of secure communication between an implanted device and an external device comprising:
inducing a single induced current in an implanted device by a nearby external device wherein the single induced current serves as both a charging current and a communication carrier;
modulating a load on said single induced current by said implanted device to transmit an encryption key;
generating noise by said nearby external device configured to obscure said modulated load;
adding by said nearby external device of said noise to said single induced current simultaneous to said modulating;
encrypting data by said implanted device using said encryption key to produce an encrypted signal; and
transmitting of said encrypted signal by the implanted device;
wherein said method further comprises said nearby external device charging a power source of said implantable device with said single induced current concurrent with said modulating and adding of noise.

22. The method of claim 21 further comprising extracting said encryption key based on said added noise; wherein said nearby external device comprises a power transmitter and said adding is by said power transmitter.

23. The method of claim 22, wherein said encryption key is transmitted over a channel said noise is added to, the channel comprising a transcutaneous energy transfer link.

\* \* \* \* \*